United States Patent [19]

Markowitz et al.

[11] Patent Number: 5,589,159
[45] Date of Patent: Dec. 31, 1996

[54] DISPERSIBLE PARTICULATE SYSTEM FOR DESENSITIZING TEETH

[75] Inventors: Kenneth Markowitz, Fanwood; Mikhail Y. Gelfer, Jersey City, both of N.J.

[73] Assignee: Block Drug Company Inc., Jersey City, N.J.

[21] Appl. No.: 419,816

[22] Filed: Apr. 11, 1995

[51] Int. Cl.⁶ .............................. A61K 7/16; A61K 7/18; A61K 47/04
[52] U.S. Cl. .................. 424/49; 424/52; 424/57; 514/770
[58] Field of Search .................... 424/49–58, 491–88

[56] References Cited

U.S. PATENT DOCUMENTS

| | | | |
|---|---|---|---|
| 4,418,053 | 11/1983 | Muhler et al. | 424/52 |
| 4,645,662 | 2/1987 | Nakashima et al. | 424/52 |
| 4,992,258 | 2/1991 | Mason | 424/49 |
| 5,240,697 | 8/1993 | Norfleet et al. | 424/52 |
| 5,328,682 | 7/1994 | Pullen et al. | 424/49 |
| 5,352,439 | 10/1994 | Norfleet et al. | 424/52 |
| 5,374,417 | 12/1994 | Norfleet et al. | 424/49 |
| 5,433,941 | 7/1995 | Patel | 424/58 |
| 5,433,956 | 7/1995 | Patel | 424/400 |
| 5,486,350 | 1/1996 | Norfleet et al. | 424/49 |

*Primary Examiner*—Shep K. Rose
*Attorney, Agent, or Firm*—Ostrolenk, Faber, Gerb & Soffen, LLP

[57] ABSTRACT

A method for treating hypersensitive teeth by treating the teeth with an oral composition comprising hectorite clay, especially Laponite clay.

16 Claims, No Drawings

DISPERSIBLE PARTICULATE SYSTEM FOR DESENSITIZING TEETH

BACKGROUND OF THE INVENTION

1. Field of the Invention

The invention is directed to new desensitizers for hypersensitive teeth and to methods of making and using such desensitizers.

2. Description of Related Art

Dentinal hypersensitivity causes pain in the mouth of a patient when a nerve in an affected tooth is exposed to certain external stimuli, including temperature and tactile stimuli. One possible source of dental hypersensitivity is that the dentin of affected teeth is over-exposed to the stimuli due to injury, disease or some other reason. Dentin generally contains channels, called tubules, that allow material and energy transport between the exterior of the dentin and the interior of the tooth where the nerve resides. Exposure of these tubules to external stimuli can cause irritation of the nerve in a tooth, leading to discomfort. Although the exact mechanism of hypersensitivity remains under investigation, recent investigations have shown that the pain triggered by air currents is related to the number of exposed tubules per unit area of dentin (Kontturi-Narhi, Dentin Hypersensitivity—Factors Related to the Occurrence of Pain Symptoms. Kuopio University Publications B. Dental Sciences 5.) According to the hydrodynamic theory of dentin sensitivity mechanical and thermal stimuli of the exposed smear layer free dentin surface, induces minute movements of the intratubular fluid. These fluid movements induce pain encoding nerve responses in the intradental nerves located near the dentin/pulp border. Recent investigations have strengthened the experimental evidence in support of this relationship (B. Matthews and N. Vongsavan Archs Oral Biol, 39 (Suppl): 875–955, 1994).

Dental hypersensitivity is generally treated by either treating the nerve in the tooth to make it less sensitive to stimuli or by blocking or occluding the tubules to prevent or limit exposure of the nerve to external stimuli and limit the stimulus triggered fluid movements in the dentinal tubules.

Treatments that directly affect the nerve generally interfere with the electrolyte balance near the nerve to affect the outer membranes of the nerve so that the nerve does not "fire" as frequently or as strongly as an untreated nerve. Useful agents in treating dental hypersensitivity in this manner include potassium nitrate, as set forth in U.S. Pat. No. 3,863,006 to Hodosh, issued Jan. 28, 1975, potassium chloride, as set forth in U.S. Pat. No. 4,751,072 to Kim, issued Jun. 14, 1988, potassium bicarbonate, as set forth in U.S. Pat. No. 4,631,185 to Kim, issued Dec. 23, 1986, and strontium chloride, as set forth in U.S. Pat. No. 3,122,483 to Rosenthal, issued Feb. 25, 1964.

Occlusion of the tubules provides an alternative method of treatment. Useful reported agents include polymeric agents such as Carbopol, as set forth in U.S. Pat. No. 5,270,031 to Lim et al., issued Dec. 14, 1993, and certain polystyrene beads, as set fort in U.S. Pat. No. 5,211,939 to Turesky et al, issued May. 18, 1993.

Apatite can also be an anti-hypersensitivity agent. U.S. Pat. No. 4,634,589 to Scheller, issued Jan. 6, 1987, and U.S. Pat. No. 4,710,372, issued Dec. 1, 1987, also to Scheller, disclose dentifrices for hypersensitive teeth containing apatite having an average particle size of less than 10 microns and optionally a local anesthetic. No other soluble mineral salts are permitted to exert any interfering effect in these patents. The apatite reduces the diameter of the dentin channels.

Montmorrolinite clay has also been reported as a desensitizing agent in U.S. Pat. No. 4,992,258 to Mason, issued Feb. 12, 1991. Unfortunately, montmorrolinite clay is not compatible with most known fluoridating agents and thus has limited use. In addition, montmorrolinite clay loses its ability to thicken a dentifrice and has reduced ability to block tubules in the presence of inorganic salts, such as potassium salts, so its use as a desensitizer is limited.

Other types of clays have been used in dental applications, although not in a desensitizing capacity. With the advent of clear gel dentifrices, hectodte clays, especially laponite clays, have been used as thickeners for dentifrices, for example as reported in U.S. Pat. No. 4,069,310 to Harrison and in Mayes, B., "Synthetic Hectoritc—A New Toothpaste Binder," International Journal of Cosmetic Science, 1,329–340 (1979). While thickeners and binders are usually found in dentifrices at about 1% by weight, the Harrison patent indicates that the thickener may be present in amounts up to 5% by weight. Indeed, the Mason patent discussed above indicates that laponite may be one of a number of thickeners used in the dentifrice, despite its teaching of montmorrolinite clay as a desensitizer.

U.S. Pat. No. 4,474,750, Gaffar et al., issued Oct. 2, 1984, discloses toothpaste, cream or gel in which the thickening agent can be Laponite CP or SP in an amount up to about 10% by weight. There is no disclosure in the patent that the Laponite is incorporated in an oral composition for the purpose of treating hypersensitive teeth.

U.S. Pat. No. 4,081,526 to Asakawa et at., issued Mar. 28, 1978, discloses dentifrice compositions comprising 0.5 to 13% of a hectoritc clay such as Laponite, for removing plaque from the teeth.

Despite the ongoing work in the field of desensitizers, a strong and long-felt need remains in the art for an effective tubule blocking agent that is compatible with fluorides and other conventional dentifrice ingredients. This agent must work well yet not be distasteful to use. It must be stable for the typical shelf life of a dentifrice, and it should be affordable.

SUMMARY OF THE INVENTION

The principal object of the present invention therefore is to provide an effective tubule blocking agent that is compatible with fluorides and other conventional dentifiice ingredients and that is also organoleptically acceptable.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides a desensitizing agent for hypersensitive teeth comprising a hectoritc clay, such as Laponite clay.

To further achieve the foregoing objects and in accordance with the purpose of the invention, the invention further provides a method for treating hypersensitive teeth by contacting the teeth with a desensitizing formulation comprising a therapeutic amount of a hectorite clay, such as Laponite clay.

DESCRIPTION OF THE PREFERRED EMBODIMENTS

Reference will now be made in detail to the presently preferred embodiments of the invention.

The invention comprises a composition for treating hypersensitive teeth, such as a dentifrice (either a paste or a gel) or other appropriate oral vehicle. The composition comprises a hectorite clay in an mount and in a formulation sufficient to desensitize teeth. Preferred hectorite clays include Laponite clays, and especially preferred are treated, so-called "synthetic" hectorite clays such as LAPONITE D® and LAPONITE DF®, both sold by Southern Clay Products, Inc. These clays have been treated to make them suitable for dental purposes (as thickeners for clear gel dentifrices), and LAPONITE DF® has been treated by the addition of fluorine to the clay to prevent absorption of fluoride from dentifrice formulations. Additional preferred Laponite clays, sold under the trade name LAPONITE®, are products of Laporte Industries Inc. Laponites are synthetic hectorite clays composed of magnesium, lithium, silica, oxygen, hydrogen, and sodium. Like other clays, Laponites are composed in the dry state of platelets arranged in stacks. Each platelet has a double layer of tetrahedral silica bonded to oxygen atoms. Between the two silica layers there is a sheet of cations composed of magnesium and lithium in a 5.3 to 0.7 ratio. These cations coordinate the inner row of silica bound oxygens and OH groups. The partial substitution of Magnesium (+2) with Lithium (+1) imparts an overall negative charge to the silica surface. The presence of incompletely complexed cations which are part of the center (Mg, Li) sheet impart a positive charge on the edges of the platelet.

Inbetween individual stacked platelets are exchangeable cations such as sodium. When a Laponite clay is properly dispersed in water, these exchangeable cations draw water into the spaces between the platelets via osmotic forces. This bulk inflow of water forces the platelets apart. When Laponite clay is properly dispersed in water in the presence of low levels of electrolytes, the anionic silica faces and the cationic edges can electrostatically attract each other. This leads to the formation of what is known as a card house structure. Shear stresses can readily disrupt this card house structure. This structure formation and disruption by shear stress means that Laponite clay dispersions have marked thixotropic properties that make them attractive as a thickening agents, especially for clear gel dentifrices.

Importantly and unexpectedly, however, concentrations and chemical environmental conditions which favor structured gel formation with Laponite clay dispersions do not necessarily favor desensitizing efficacy. Compositions in which Laponite clays are dispersed so as to prevent or hinder the formation of gel structure demonstrate superior performance in desensitizing capability, as measured by tubule blocking experiments. Such compositions typically use higher mounts of clay than found with compositions manifesting ideal gel structures. In addition, inorganic dispersants and organic polymeric dispersants enhance the desensitizing performance of the Laponite clay. Laponite clay-containing compositions with such added dispersants have superior efficacy, demonstrate pleasant organoleptic characteristics, and are compatible with fluoride and most other dentifrice ingredients.

Fluoride treated Laponite clays are preferred for their ability to coexist with fluoride in a dentifrice. Dentifrices and mixtures containing fluoride sources and hectorite clays or fluoride treated Laponite clays were examined for fluoride bioavailability, and dentifrices containing untreated hectorite clays reduced sodium fluoride availability, while fluoride treated Laponite clay dentifrices retained full fluoride bioavailability.

Preferably the dentifrice formulation is in the form of a paste or a gel that comprises from about 0.1% by weight to about 25% by weight of clay. More preferably, the clay comprises from about 1% clay to about 20% by weight of the clay, and, most preferably from about 2% to about 15%. The clay may also be incorporated into other oral care formulations such as mouth rinses, as well as dentifrice formulations.

The flow reducing efficacy of the clay can surprisingly be improved by adding dispersants such as salts, thickeners, or other additives. Preferred salts include: potassium salts, strontium salts (especially preferred salts include desensitizing salts, such as potassium nitrate, potassium chloride, potassium bicarbonate and strontium chloride), and pyrophosphate salts, especially potassium and sodium tetrapyrophosphate salts and potassium and sodium acid pyrophosphate salts. Preferred thickeners include polymeric thickeners, and especially preferred are cellulosic thickeners, including ionically modified cellulosic polymers such as sodium carboxymethyl cellulose, a product of Aqualon, and a cationically modified cellulosic polymer known as CELQUAT®, a product of National Starch and Chemical Company. When tested by itself, the CELQUAT® polymer induced inconsistent dentin fluid flow reductions as measured using the technique set out in the examples. In contrast, when tested a part of a prototype dentifrice containing a hectorite clay, consistently high flow reductions were observed.

Although the inventors do not wish to be bound by any theory, it appears that hectorite clays, especially Laponite clays, comprise a plurality of individual mineral platelets having positively charged edges and negatively charged flat faces. It seems that the cationically charged modified cellulose and other positively charged entities can interact with the artionic face of the clay, resulting in better dispersion of the clay leading to a particle size appropriate for penetrating dentin tubules, and a modification of the electrochemical chacteristics of the particle resulting in enhanced electrostatic adherence of the clay to the tubule wall. Aspects of clay chemistry are discussed in more detail in the Mayes article mentioned above and in U.S. Pat. No. 4,621,070 to Pinnavaia et al., issued Nov. 4, 1986.

Oral rinses using the clay can be in the form of oral solutions or dispersions. Oral rinses may contain conventional flavors, colorants and other additives having organoleptic or therapeutic efficacy.

Dentifrices made using the hectorite clay will usually be water-based and will contain a humectant such as glycerin, sorbitol or other sugar alcohol, propylene glycol or polyethylene glycol. The dentifrice may be a paste or a gel. The gelling agent may be an alkali metal carboxymethyl cellulose, hydroxy ethyl cellulose or hydroxy methyl cellulose, xanthan gum, viscarin, iota carrageenan, gelatin, starch, glucose, sucrose, polyvinyl pyrollidone, polyvinyl alcohol, gum tragacanth, gum daraya, hydroxy propyl cellulose, methyl cellulose and sodium alginate, and magnesium aluminum silicate gel. Preferred are those agents that are compatible with fluoride.

Additional agents useful in a dentifrice are polishing agents such as precipitated silica, hydrated silica and other known abrasive polishing agents, fluoride, detergents, coloring or whitening agents such as titanium dioxide, fragrances and flavorings. Additional therapeutic agents, such as tartar control agents, antibacterial agents such as triclosan or chlorhexadine, may also be added.

A dentifrice in accordance with the invention may be made by mixing the ingredients in any conventional manner, for example by creating a gel with the water and gelling agent and then adding the water soluble ingredients. Finally, a surfactant is added and the hydrophobic ingredients are then added. The mixture is then packaged in a convention dentifrice container such as a tube, and applied to the surface of the teeth through conventional brushing, coating, painting or other direct or indirect application technique.

The benefits of the invention will be demonstrated in the following examples.

EXAMPLES

Test Procedures

Dispersions of hectodte clays in water with various ingredients and prototype dentifrices containing hectorite clays were tested using an in vitro model of dentin sensitivity first described by Pashley (J. Periodontology, Vol. 55, No. 9, p.522, September 1984). U.S. Pat. No. 5,270,031 to Lim et al, issued Dec. 14, 1993, also describes this methodology.

In this method, intact human molars free of caries or restorations are sectioned perpendicular to the long axis of the tooth with a metallurgical saw into thin sections about 0.4 to 0.6 mm thick. Sections containing dentin and free of enamel are retained for testing. These sections are then etched with a EDTA (ethylenediamine tetra acetic acid) solution to remove the smear layer. The disc is mounted on a split chamber device as reported in J. Dent. Research, 57:187 (1978). This special leak proof chamber is connected to a pressurized fluid reservoir containing a tissue culture fluid. By using a mixture of pressurized $N_2$ and $CO_2$ gas, the fluid can be maintained at physiological pH. To further ensure accuracy, the disks are wetted with human saliva to approximate the intraoral condition. The apparatus includes a glass capillary tube mounted on a ruler or other measuring instrument. An air bubble is injected into the glass capillary tube. By measuring the displacement of this bubble as a function of time, the fluid flow through the dentin disk can be measured. (It has been reported that fluid actually flows out of dentin tubules from the interior of a normal human tooth.)

Following measurement of the baseline fluid flow in the dentin disk, the experimental mixture or dentifrice is applied to the external disk surface with a nylon brush. After a defined period of brushing, the experimental material is rinsed off, and the post application hydraulic conductance is measured. In this fashion, the ability of various experimental materials, both alone and as components of dentifrice systems, can be tested for the ability to obstruct fluid flow in the dentinal tubules. The percent flow reduction induced by brushing with experimental materials can then be calculated.

Examples 1–5

Combinations of Laponite clays with water and other specified ingredients were prepared and tested for flow reduction using the method set forth above. Each combination had the composition set out in Table 1 and had the flow reduction shown in Table 1. The examples show the good dentin fluid flow reducing ability of hectorite clays, especially when the clay is associated with a dispersant, such as a polymeric dispersant or salts.

TABLE 1

| | Percent flow reduction with aqueous combinations of Laponites | |
|---|---|---|
| EXAMPLE | TREATMENT | POST APPLICATION FLUID FLOW REDUCTION |
| 1 | 5% LAPONITE D | 55.3% |
| 2 | 5% LAPONITE DF, 0.25% NaF | 48.0% |
| 3 | 5% LAPONITE DF, 5% $KNO_3$ | 54.2% |
| 4 | 5% LAPONITE DF, 5% $KNO_3$, 4% Carboxymethyl cellulose, 0.25% NaF | 83.4% |
| 5 | 5% LAPONITE DF in 5% $KNO_3$, 0.25% NaF, cationic cellulose polymer CELQUAT 240 SC(8%) | 96.0% |

Examples 6–13

The following dentifrice formulations were prepared in the following manner. Into a suitable mixer, equipped with a vacuum system, such as whipmixer for the laboratory scale or Koruma mixer for larger (pilot plant) batches, the required amount of purified water is added. Key ingredients such as sodium fluoride (or sodium MFP), tetrapotassium pyrophosphate, trisodium phosphate, potassium or strontium salts, as appropriate, are added to the mixer, followed by sodium saccharin, silicon dioxide and LAPONITE DF. The above bulk was mixed for approximately 10–30 minutes (under vacuum) followed by the addition of abrasives, gum pre-mix (humectant and gums), flavor and detergents. Final mixing of 20–30 minutes was conducted under vacuum to deaerate the product.

Example 6

| Ingredient | Weight Percent |
|---|---|
| Laponite DF | 5.0 |
| Sodium fluoride | 0.24 |
| Sorbitol solution | 20.0 |
| Glycerin | 20.0 |
| Silicon dioxide | 1.0 |
| Amorphous silica | 10.0 |
| Carboxymethylcellulose | 1.5 |
| Carbomer | 0.1 |
| Sodium saccharin | 0.3 |
| Titanium dioxide | 0.5 |
| Cocoamidopropylbetaine | 5.0 |
| Trisodium phosphate, anhydrous | 1.0 |
| Flavor | 1.5 |
| Purified water | Q.S. to 100.0 |

Example 7

| Ingredient | Weight Percent |
|---|---|
| Laponite DF | 8.0 |
| Sodium fluoride | 0.32 |
| Potassium chloride | 4.0 |
| Hydrated silica | 10.0 |
| Hydroxyethylcellulose | 1.5 |
| Sodium saccharin | 0.3 |
| Sodium lauryl sulfate | 1.5 |

-continued

| Ingredient | Weight Percent |
| --- | --- |
| Triclosan | 0.3 |
| Sorbitol solution | 40.0 |
| Flavor | 1.3 |
| Purified water | Q.S. to 100.0 |

Example 8

| Ingredient | Weight Percent |
| --- | --- |
| Lapinite DF | 6.0 |
| Sodium MFP | 0.8 |
| Silicon dioxide | 2.0 |
| Dicalcium phosphate dihydrate | 30.0 |
| Carboxymethylcellulose | 1.0 |
| Sodium saccharin | 0.25 |
| Titanium dioxide | 0.5 |
| Cocoamidopropylbetaine | 7.0 |
| Sodium cocomethyl acid taurate | 0.75 |
| Trisodium phosphate, anhydrous | 1.0 |
| Sorbitol solution | 10.0 |
| Glycerin | 25.0 |
| Flavor | 1.2 |
| Purified water | Q.S. to 100.0 |

Example 9

| Ingredient | Weight Percent |
| --- | --- |
| Laponite DF | 7.5 |
| Sodium MFP | 0.8 |
| Silicon dioxide | 1.0 |
| Calcium carbonate | 15.0 |
| Carboxymethylcellulose | 1.0 |
| Carbomer | 0.1 |
| Sodium saccharin | 0.3 |
| Titanium dioxide | 0.5 |
| Sodium lauryl sulfate | 1.5 |
| Disodium pyrophosphate | 0.3 |
| Sorbitol solution | 30.0 |
| Glyverin | 10.0 |
| Flavor | 1.3 |
| Purified water | Q.S. to 100.0 |

Example 10

| Ingredient | Weight Percent |
| --- | --- |
| Laponite DF | 5.0 |
| Potassium chloride | 3.75 |
| Sodium fluoride | 0.24 |
| Silicon dioxide | 1.5 |
| Amorphous silica | 10.0 |
| Carboxymethylcellulose | 2.0 |
| Carbomer | 0.1 |
| Sodium saccharin | 0.35 |
| Titanium oxide | 0.5 |
| Cocoamidopropylbetaine | 6.0 |
| Sodium cocomethyl acid taurate | 0.5 |
| Tetrapotassium pyrophosphate | 3.0 |
| Triclosan | 0.3 |
| Flavor | 1.3 |
| Sorbitol solution | 40.0 |
| Purified water | Q.S. to 100.0 |

Example 11

| Ingredient | Weight Percent |
| --- | --- |
| Laponite DF | 5.0 |
| Sodium Fluoride | 0.243 |
| Tetrapotassium pyrophosphate | 3.0 |
| Potassium citrate | 5.0 |
| Hydrated Silica | 12.0 |
| Hydroxyethylcellulose | 1.4 |
| Sodium saccharin | 0.3 |
| Sodium cocomethyl acid taurate | 1.5 |
| Trisodium phosphate, anhydrous | 0.5 |
| Sorbitl solution | 12.0 |
| Glycerin | 12.0 |
| Flavor | 1.2 |
| Purified Water | Q.S. to 100.0 |

Example 12

| Ingredient | Weight Percent |
| --- | --- |
| Laponite DF | 5.0 |
| Sodium fluoride | 0.243 |
| Tetrapotassium pyrophosphate | 3.0 |
| Potassium bicarbonate | 3.0 |
| Hydrated silica | 12.0 |
| Hydroxyethylcellulose | 1.4 |
| Sodium saccharin | 0.3 |
| Sodium cocomethyl acid taurate | 1.5 |
| Trisodium phosphate, anhydrous | 0.5 |
| Sorbitol solution | 12.0 |
| Glycerin | 12.0 |
| Flavor | 1.2 |
| Purified water | Q.S. to 100.0 |

Example 13

| Ingredient | Weight Percent |
| --- | --- |
| Laponite DF | 6.0 |
| Strontium chloride hexahydrate | 10.0 |
| Silicon dioxide | 1.0 |
| Hydrated silica | 12.0 |
| Sodium saccharin | 0.3 |
| Titanium dioxide | 1.0 |
| Carboxymethylcellulose | 1.5 |
| Sodium cocomethyl acid taurate | 1.2 |
| Sorbitol solution | 12.0 |
| Glycerin | 12.0 |
| Flavor | 1.2 |
| Purified water | Q.S. to 100.0 |

Several of the dentifrice formulations described above were tested for their ability to reduce dentin fluid flow. The results of this testing are set out in Table 2.

TABLE 2

Percent flow reduction for selected dentifrices

| Example Number | Principal Ingredient | % Flow Reduction |
| --- | --- | --- |
| Example 6 | Laponite (5%), NaF (0.24%) | 79% |
| Example 7 | Laponite (8%); NaF (0.32%) | 82% |
| Example 10 | Laponite (5%); NaF (0.24%) Tetrapotassium pyrophosphate (3%) | 87% |

The purpose of the above description is to illustrate some embodiments of the present invention without implying a limitation. It will apparent to those skilled in the art that various modifications and variations may be made in the apparatus or procedure of the invention without departing from the scope or spirit of the invention.

What is claimed is:

1. In a composition for treating hypersensitive teeth comprising an effective desensitizing amount of a desensitizing agent and a carrier therefor, the improvement which comprises the desensitizing agent being hectorite clay.

2. The composition of claim 1, wherein said clay is Laponite clay.

3. The composition of claim 2, wherein said clay contains fluoride.

4. The composition of claim 1, further comprising a dispersant.

5. The composition of claim 4, wherein said dispersant is a salt.

6. The composition of claim 5, wherein said ionic salt is an alkali salt.

7. The composition of claim 5, wherein said salt is selected from the group consisting of alkali salts of pyrophosphates, nitrates, halides, citrates, carbonates, bicarbonates, and strontium salts and mixtures thereof.

8. The composition of claim 4, wherein said dispersant is a cellulosic compound.

9. The composition of claim 8, wherein said cellulosic compound is cationically modified.

10. The composition of claim 9, wherein said cellulosic compound comprises a cationically modified cellulose.

11. The composition of claim 10, further comprising a salt.

12. The composition of claim 11, wherein said salt is an alkali salt.

13. The composition of claim 12, wherein said salt is selected from the group consisting of alkalai salts of pyrophosphates, nitrates, halides, citrates, carbonates, bicarbonates, and strontium salts and mixtures thereof.

14. A method for treating a hypersensitive tooth, comprising administering to said tooth a therapeutically effective mount of the composition of claim 1.

15. A method for treating a hypersensitive tooth, comprising administering to said tooth a therapeutically effective amount of the composition of claim 1.

16. In the method of blocking, occluding, or sealing dentinal tubules in hypersensitive teeth the improvement consisting essentially of the step of blocking said tubules in said hypersensitive teeth with fluoride oral rinses or fluoride dentifrice pastes or gels containing fluoride treated Laponite or hectorite clay as the essential hypersensitive teeth dentinal tubule blocking agent.

* * * * *